US006479266B1

(12) United States Patent
Rothe et al.

(10) Patent No.: US 6,479,266 B1
(45) Date of Patent: *Nov. 12, 2002

(54) IKK-α PROTEINS NUCLEIC ACIDS AND METHODS

(75) Inventors: Mike Rothe, San Mateo, CA (US); Zhaodan Cao, Pacifica, CA (US); Catherine Régnier, South San Francisco, CA (US)

(73) Assignee: Tularik Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/109,986

(22) Filed: Jul. 2, 1998

Related U.S. Application Data

(63) Continuation-in-part of application No. 08/890,854, filed on Jul. 10, 1997, which is a continuation of application No. 08/887,115, filed on Jul. 1, 1997, now abandoned.

(51) Int. Cl.$^7$ ................................................. C12N 9/12
(52) U.S. Cl. ......................................... 435/194; 435/15
(58) Field of Search .................................... 435/194, 15

(56) References Cited

U.S. PATENT DOCUMENTS 6,268,194 B1 * 7/2001 Karin et al. ................. 435/194

OTHER PUBLICATIONS

Chen et al., 1996 Cell 84:853–62.
Regnier et al., 1997 Cell 90:373–83.
Connelly et al., 1995 Cell. Mol. Biol. Res. 41:537–49.
Hillier et al. 1996 EST #AA047396 WashU–Merck EST Project.

Mock, B.A., et al. CHUK, A Conserved Helix–Loop–Helix Ubiquitous Kinase, Maps To Human Chromosome 10 And Mouse Chromosome 19. Genomics. 1995, vol. 27, pp. 348–351.

Traenchner, E.B–M.et al. Phosphorylation of Human IκB–Alpha On Serines 32 and 36 Controls IκB–Alpha Proteolysis and NF–κB Activation in Response To Diverse Stimuli. EMBO J. 1995, vol. 14, No. 12, pp. 2876–2883.

Didonato, J., et al. Mapping of The Inducible IκB Phosphorylation Sites That Signal Its Ubiquitination And Degradation. Mol Cell. Biol. Apr. 1996, vol. 16, No. 4, pp. 1295–1304.

Lee, F.S, et al. Activation Of The IκB Alpha Kinase Complex By MEKK1, A Kinase Of The JNK Pathway. Cell. Jan. 24, 1997, vol. 88, pp. 213–222.

* cited by examiner

*Primary Examiner*—Charles L. Patterson, Jr.
(74) *Attorney, Agent, or Firm*—Richard Aron Osman

(57) ABSTRACT

The invention provides methods and compositions relating to an IκB kinase, IKK-α, and related nucleic acids. The polypeptides may be produced recombinantly from transformed host cells from the disclosed IKK-α encoding nucleic acids or purified from human cells. The invention provides isolated IKK-α hybridization probes and primers capable of specifically hybridizing with the disclosed IKK-α genes, IKK-α-specific binding agents such as specific antibodies, and methods of making and using the subject compositions in diagnosis, therapy and in the biopharmaceutical industry.

20 Claims, No Drawings

IKK-α PROTEINS NUCLEIC ACIDS AND METHODS

This is a continuing application of U.S. Ser. No. 08/890,854, filed Jul. 10, 1997, which is a continuing application under 35USC120 of U.S. Ser. No. 08/887,115, now abandoned, filed Jul. 1, 1997.

FIELD OF THE INVENTION

The field of this invention is proteins involved in transcription factor activation.

BACKGROUND

Cytokines trigger changes in gene expression by modifying the activity of otherwise latent transcription factors (Hill and Treisman, 1995). Nuclear factor κB (NF-κB) is a prominent example of how such an external stimulus is converted into an active transcription factor (Verma et al., 1995). The NF-κB system is composed of homo- and heterodimers of members of the Rel family of related transcription factors that control the expression of numerous immune and inflammatory response genes as well as important viral genes (Lenardo and Baltimore, 1989; Baeuerle and Henkel, 1994). The activity of NF-κB transcription factors is regulated by their subcellular localization (Verma et al., 1995). Inmost cell types, NF-κB is present as a heterodimer comprising of a 50 kDa and a 65 kDa subunit. This heterodimer is sequestered in the cytoplasm in association with IκBα a member of the IκB family of inhibitory proteins (Finco and Baldwin, 1995; Thanos and Maniatis, 1995; Verma et al., 1995). IκBα masks the nuclear localization signal of NF-κB and thereby prevents NF-κB nuclear translocation. Conversion of NF-κB into an active transcription factor that translocates into the nucleus and binds to cognate DNA sequences requires the phosphorylation and subsequent ubiquitin-dependent degradation of IκBα in the 26s proteasome. Signal-induced phosphorylation of IκBα occurs at serines 32 and 36. Mutation of one or both of these serines renders IκBα resistant to ubiquitination and proteolytic degradation (Chen et al., 1995).

The pleiotropic cytokines tumor necrosis factor (TNF) and interleukin-1 (IL-1) are among the physiological inducers of IκB phosphorylation and subsequent NF-κB activation (Osborn et al., 1989; Beg et al., 1993). Although TNF and IL-1 initiate signaling cascades leading to NF-κB activation via distinct families of cell-surface receptors (Smith et al., 1994; Dinarello, 1996), both pathways utilize members of the TNF receptor-associated factor (TRAF) family of adaptor proteins as signal transducers (Rothe et al., 1995; Hsu et al., 1996; Cao et al., 1996b). TRAF proteins were originally found to associate directly with the cytoplasmic domains of several members of the TNF receptor family including the 75 kDa TNF receptor (TNFR2), CD40, CD30, and the lymphotoxin-β receptor (Rothe et al., 1994; Hu et al., 1994; Cheng et al., 1995; Mosialos et al., 1995; Song and Donner, 1995; Sato et al., 1995; Lee et al., 1996; Gedrich et al., 1996; Ansieau et al., 1996). In addition, TRAF proteins are recruited indirectly to the 55 kDa TNF receptor (TNFR1) by the adaptor protein TRADD (Hsu et al., 1996). Activation of NF-κB by TNF requires TRAF2 (Rothe et al., 1995; Hsu et al., 1996). TRAF5 has also been implicated in NF-κB activation by members of the TNF receptor family (Nakano et al., 1996). In contrast, TRAF6 participates in NF-κB activation by IL-1 (Cao et al., 1996b). Upon IL-1 treatment, TRAF6 associates with IRAK, a serine-threonine kinase that binds to the IL-1 receptor complex (Cao et al., 1996a).

The NF-κB-inducing kinase (NIK) is a member of the MAP kinase kinase kinase (MAP3K) family that was identified as a TRAF2-interacting protein (Malinin et al., 1997). NIK activates NF-κB when overexpressed, and kinase-inactive mutants of NIK comprising its TRAF2-interacting C-terminal domain (NIK$_{(624-947)}$) or lacking two crucial lysine residues in its kinase domain (NIK$_{(KK429-430AA)}$) behave as dominant-negative inhibitors that suppress TNF-, IL-1-, and TRAF2-induced NF-κB activation (Malinin et al., 1997). Recently, NIK was found to associate with additional members of the TRAF family, including TRAF5 and TRAF6. Catalytically inactive mutants of NIK also inhibited TRAF5- and TRAF6-induced NF-κB activation, thus providing a unifying concept for NIK as a common mediator in the NF-κB signaling cascades triggered by TNF and IL-1 downstream of TRAFs.

Here, we disclose a novel human kinase IκB Kinase, IKK-α, as a NIK-interacting protein. IKK-α has sequence similarity to the conceptual translate of a previously identified open reading frame (SEQ ID NO:5) postulated to encode a serine-threonine kinase of unknown function ('Conserved Helix-loop-helix Ubiquitous Kinase' or CHUK, Connelly and Marcu, 1995; Mock et al., 1995). Catalytically inactive mutants of IKK-α are shown to suppress NF-κB activation induced by TNF and IL-1 stimulation as well as by TRAF and NIK overexpression; transiently expressed IKK-α is shown to associate with the endogenous IκBα complex; and IKK-α is shown to phosphorylate IκBα on serines 32 and 36.

SUMMARY OF THE INVENTION

The invention provides methods and compositions relating to isolated IKK-α polypeptides, related nucleic acids, polypeptide domains thereof having IKK-α-specific structure and activity and modulators of IKK-α function, particularly IκB kinase activity. IKK-α polypeptides can regulate NFκB activation and hence provide important regulators of cell function. The polypeptides may be produced recombinantly from transformed host cells from the subject IKK-α polypeptide encoding nucleic acids or purified from mammalian cells. The invention provides isolated IKK-α hybridization probes and primers capable of specifically hybridizing with the disclosed IKK-α gene, IKK-α-specific binding agents such as specific antibodies, and methods of making and using the subject compositions in diagnosis (e.g. genetic hybridization screens for IKK-α transcripts), therapy (e.g. IKK-α kinase inhibitors to inhibit TNF signal transduction) and in the biopharmaceutical industry (e.g. as immunogens, reagents for isolating other transcriptional regulators, reagents for screening chemical libraries for lead pharmacological agents, etc.).

DETAILED DESCRIPTION OF THE INVENTION

The nucleotide sequence of a natural cDNA encoding a human IKK-α polypeptide is shown as SEQ ID NO:3, and the full conceptual translate is shown as SEQ ID NO:4. The IKK-α polypeptides of the invention include incomplete translates of SEQ ID NO:3, particularly of SEQ ID NO:3, residues 1–638, which translates and deletion mutants of SEQ ID NO:4 have human IKK-α-specific amino acid sequence, binding specificity or function and comprise at least one of Cys30, Leu403, Glu543, Leu604, Thr679, Ser680, Pro684, Thr686 and Ser687. Preferred translates/deletion mutants comprise at least a 6, preferably at least a 12, more preferably at least an 18 residue Cys30, Leu403, Glu543, Leu604, Thr679, Ser680, Pro684, Thr686 or Ser687-containing domain of SEQ ID NO:4, preferably including at least 8, more preferably at least 12, most preferably at least 20 contiguous residues which immediately flank said residue on one, preferably both sides, with said residue preferably residing within said contigous residues, see, e.g. Table 1A, which mutants provide hIKK-α specific epitopes and immunogens.

TABLE 1A. Exemplary IKK-α polypeptides having IKK-α binding specificity

αΔ1(SEQ ID NO:4, residues 1–30)
αΔ2(SEQ ID NO:4, residues 22–31)
αΔ3(SEQ ID NO:4, residues 599–608)
αΔ4(SEQ ID NO:4, residues 601–681)
αΔ5(SEQ ID NO:4, residues 604–679)
αΔ6(SEQ ID NO:4, residues 670–687)
αΔ7(SEQ ID NO:4, residues 679–687)
αΔ8(SEQ ID NO:4, residues 680–690)
αΔ9(SEQ ID NO:4, residues 684–695)
αΔ10(SEQ ID NO:4, residues 686–699)
αΔ11(SEQ ID NO:4, residues 312–345)
αΔ12(SEQ ID NO:4, residues 419–444)
αΔ13(SEQ ID NO:4, residues 495–503)
αΔ14(SEQ ID NO:4, residues 565–590)
αΔ15(SEQ ID NO:4, residues 610–627)
αΔ16(SEQ ID NO:4, residues 627–638)
αΔ17(SEQ ID NO:4, residues 715–740)
αΔ18(SEQ ID NO:4, residues 737–745)

In a particular embodiment, the invention provides IKK-αGlu$^{543}$ polypeptides, IKK-αGlu$^{543}$ polypeptide-encoding nucleic acids/polynucleotides, and IKK-αGlu$^{543}$ polypeptide-based methods (below), which IKK-αGlu$^{543}$ polypeptides comprise at least 8, preferably at least 10, more preferably at least 12, more preferably at least 16, most preferably at least 24 consecutive amino acid residues of the amino acid sequence set forth as SEQ ID NO:4, which consecutive amino acid residues comprise the amino acid residue 543 (Glu) of SEQ ID NO:4. Exemplary IKK-αGlu$^{543}$ polypeptides having IKK-αGlu$^{543}$ binding specificity and immunologically distinguishable from IKK-αGly$^{543}$ are shown in Table 1B.

TABLE 1B. Exemplary IKK-αGlu$^{543}$ polypeptides having IKK-αGlu$^{543}$ binding specificity αΔ19(SEQ ID NO:4, residues 540–548)
αΔ20(SEQ ID NO:4, residues 543–550)
αΔ21(SEQ ID NO:4, residues 536–543)
αΔ22(SEQ ID NO:4, residues 534–554)
αΔ23(SEQ ID NO:4, residues 533–543)
αΔ24(SEQ ID NO:4, residues 543–563)
αΔ25(SEQ ID NO:4, residues 542–549)
αΔ26(SEQ ID NO:4, residues 538–545)
αΔ27(SEQ ID NO:4, residues 541–547)
αΔ28(SEQ ID NO:4, residues 403–543)
αΔ29(SEQ ID NO:4, residues 403–604)
αΔ30(SEQ ID NO:4, residues 403–679)
αΔ31(SEQ ID NO:4, residues 403–680)
αΔ32(SEQ ID NO:4, residues 403–687)
αΔ33(SEQ ID NO:4, residues 543–604)
αΔ34(SEQ ID NO:4, residues 543–679)
αΔ35(SEQ ID NO:4, residues 543–684)
αΔ36(SEQ ID NO:4, residues 543–687)

The subject domains provide IKK-α domain specific activity or function, such as IKK-α-specific kinase or kinase inhibitory activity, NIK-binding or binding inhibitory activity, IκB-binding or binding inhibitory activity, NFκB activating or inhibitory activity or antibody binding. Preferred domains phosphorylate at least one and preferably both the serine 32 and 36 of IκB (Verma, I. M., et al. (1995)). As used herein, Ser32 and Ser36 of IκB refers collectively to the two serine residues which are part of the consensus sequence DSGL/IXSM/L (e.g. ser 32 and 36 in IκBα, ser 19 and 23 in IκBβ, and ser 157 and 161, or 18 and 22, depending on the usage of methionines, in IκBε, respectively.

IKK-α-specific activity or function may be determined by convenient in vitro, cell-based, or in vivo assays: e.g. in vitro binding assays, cell culture assays, in animals (e.g. gene therapy, transgenics, etc.), etc. Binding assays encompass any assay where the molecular interaction of an IKK-α polypeptide with a binding target is evaluated. The binding target may be a natural intracellular binding target such as an IKK-α substrate, a IKK-α regulating protein or other regulator that directly modulates IKK-α activity or its localization; or non-natural binding target such a specific immune protein such as an antibody, or an IKK-α specific agent such as those identified in screening assays such as described below. IKK-α-binding specificity may assayed by kinase activity or binding equilibrium constants (usually at least about $10^7 M^{-1}$, preferably at least about $10^8 M^{-1}$, more preferably at least about $10^9 M^{-1}$), by the ability of the subject polypeptide to function as negative mutants in IKK-α-expressing cells, to elicit IKK-α specific antibody in a heterologous host (e.g. a rodent or rabbit), etc. In any event, the IKK-α binding specificity of the subject IKK-α polypeptides necessarily distinguishes the murine and human CHUK sequences of Connelly and Marcu (1995) as well as IKK-β (SEQ ID NO:4).

The claimed IKK-α polypeptides are isolated or pure: an "isolated" polypeptide is unaccompanied by at least some of the material with which it is associated in its natural state, preferably constituting at least about 0.5%, and more preferably at least about 5% by weight of the total polypeptide in a given sample and a pure polypeptide constitutes at least about 90%, and preferably at least about 99% by weight of the total polypeptide in a given sample. In a particular embodiments, IKK-α polypeptides are isolated from a MKP-1 precipitable complex, isolated from a IKK complex, and/or isolated from IKK-β. The IKK-α polypeptides and polypeptide domains may be synthesized, produced by recombinant technology, or purified from mammalian, preferably human cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art.

The invention provides binding agents specific to IKK polypeptides, preferably the claimed IKK-α polypeptides, including substrates, agonists, antagonists, natural intracellular binding targets, etc., methods of identifying and making such agents, and their use in diagnosis, therapy and pharmaceutical development. For example, specific binding agents are useful in a variety of diagnostic and therapeutic applications, especially where disease or disease prognosis is associated with improper utilization of a pathway involving the subject proteins, e.g. NF-κB activation. Novel IKK-specific binding agents include IKK-specific receptors, such as somatically recombined polypeptide receptors like specific antibodies or T-cell antigen receptors (see, e.g. Harlow and Lane (1988) Antibodies, A Laboratory Manual, Cold Spring Harbor Laboratory) and other natural intracellular binding agents identified with assays such as one-, two- and three-hybrid screens, non-natural intracellular binding agents identified in screens of chemical libraries such as described below, etc. Agents of particular interest modulate IKK function, e.g. IKK-dependent transcriptional activation. For example, a wide variety of inhibitors of IKK IκB kinase activity may be used to regulate signal transduction involving IκB. Exemplary IKK IκB kinase inhibitors include known classes of serine/threonine kinase (e.g. PKC) inhibitors such as competitive inhibitors of ATP and substrate binding, antibiotics, IKK-derived peptide inhibitors, etc., see Tables II and III. IKK specificity and activity are readily quantified in high throughput kinase assays using panels of protein kinases (see cited references and Examples).

Preferred inhibitors include natural compounds such as staurosporine (Omura S, et al. J Antibiot (Tokyo) 1995 July;48(7):535–48), produced by a marine organism, and synthetic compounds such as PD 153035, which also potently inhibits the EGF receptor protein kinase (Fry DW et al. Science 1994 August 19;265(5175):1093–5). Members of the tyrphostin family of synthetic protein kinase inhibitors are also useful; these include compounds which are pure ATP competitors, compounds which are pure substrate competitors, and compounds which are mixed competitors: compete with both ATP and substrate (Levitzki A and Gazit A, Science 1995 March 24;267(5205):1782–8). Additional IKK inhibitors include peptide-based substrate competitors endogenously made by the mammalian cell, e.g. PKI (protein kinase inhibitor, Seasholtz AF et al., Proc Natl Acad Sci USA 1995 February 28;92(5):1734–8), or proteins inhibiting cdc kinases (Correa-Bordes J and Nurse P, Cell 1995 December 15;83(6):1001–9). Additional small peptide based substrate competitive kinase inhibitors and allosteric inhibitors (inhibitory mechanisms independent of ATP or substrate competition) are readily generated by established methods (Hvalby O, et al. Proc Natl Acad Sci USA 1994 May 24;91(11):4761–5; Barja P, et al., Cell Immunol 1994 January;153(1):28–38; Villar-Palasi C, Biochim Biophys Acta 1994 December 30;1224(3):384–8; Liu W Z, et al., Biochemistry 1994 August 23;33(33):10120–6).

TABLE II

Selected Small Molecule IKK Kinase Inhibitors

| HA-100[1] | Iso-H7[12] | A-3[18] |
| Chelerythrine[2] | PKC 19-31 | HA1004[19,20] |
| Staurosporine[3,4,5] | H-7[12,3,14] | K-252a[16,5] |
| Calphostin C[6,7,8,9] | H-89[15] | KT5823[16] |
| K-252b[10] | KT5720[16] | ML-9[21] |
| PKC 19-36[11] | cAMP-depPKinhib[17] | KT5926[22] |

Citations
[1]Hagiwara, M,. et al. Mol. Pharmacol. 32: 7(1987)
[2]Herbert, J. M., et al. Biochem Biophys Res Com 172: 993 (990)
[3]Schachtele, C., et al. Biochem Biophys Res Com 151: 542 (1988)
[4]Tamaoki, T., et al. Biochem Biophys Res Com 135: 397 (1986)
[5]Tischler, A. S., et al. J. Neurochemistry 55: 1159 (1990)
[6]Bruns, R. F., et al. Biochem Biophys Res Com 176: 288 (1991)
[7]Kobayashi, E., et al. Biochem Biophys Res Com 159: 548 (1989)
[8]Tamaoki, T., et al Adv2nd Mass Phosphoprotein Res 24: 497 (1990)
[9]Tamaoki, T., et al. Biotechnology 8: 732 (1990)
[10]Yasuzawa, T. J. Antibiotics 39: 1972 (1986)
[11]House, C., et al. Science 238: 1726 (1987)

TABLE II-continued

Selected Small Molecule IKK Kinase Inhibitors

[12]Quick, J., et al. Biochem. Biophys. Res. Com. 167: 657 (1992)
[13]Bouli, N. M. and Davis, M. Brain Res. 525: 198 (1990)
[14]Takahashi, I., et al. J. Pharmacol. Exp. Ther. 255: 1218 (1990)
[15]Chijiwa, T., et al J. Biol. Chem. 265: 5267 (1990)
[16]Kase, H., et al. Biochem. Biophys. Res. Com. 142: 436 (1987)
[17]Cheng, H. C., et al. J. Biol. Chem. 261: 989 (1986)
[18]Inagaki, M., et al. Mol. Pharmacol. 29: 577 (1986)
[19]Asano, T. and Hidaka, H. J Pharmaco. Exp Ther 231: 141 (1984)
[20]Hidaka, H., et al. Biochemistry 23: 5036 (1984)
[21]Nagatsu, T., et al. Biochem Biophys Res Com 143: 1045 (1987)
[22]Nakanishi S., et al. Mol. Pharmacol. 37: 428 (1990)

TABLE III

Selected Peptidyl IKK Kinase Inhibitors

| hIκBα, residues 24–39, 32Ala | hIKK-α, Δ5–203 |
| hIκBα, residues 29–47, 36Ala | hIKK-α, Δ1–178 |
| hIκBα, residues 26–46, 32/36Ala | hIKK-α, Δ368–756 |
| hIκBβ, residues 25–38, 32Ala | hIKK-α, Δ460–748 |
| hIκBβ, residues 30–41, 36Ala | hIKK-α, Δ1–289 |
| hIκBα, residues 26–46, 32/36Ala | hIKK-α, Δ12–219 |
| hIκBε, residues 24–40, 32Ala | hIKK-α, Δ307–745 |
| hIκBε, residues 31–50, 36Ala | hIKK-α, Δ319–644 |
| hIκBε, residues 27–44, 32/36Ala | |

Accordingly, the invention provides methods for modulating signal transduction involving IκB in a cell comprising the step of modulating IKK kinase activity, e.g. by contacting the cell with a serine/threonine kinase inhibitor. The cell may reside in culture or in situ, i.e. within the natural host. Preferred inhibitors are orally active in mammalian hosts. For diagnostic uses, the inhibitors or other IKK binding agents are frequently labeled, such as with fluorescent, radioactive, chemiluminescent, or other easily detectable molecules, either conjugated directly to the binding agent or conjugated to a probe specific for the binding agent.

The amino acid sequences of the disclosed IKK-α polypeptides are used to back-translate IKK-α polypeptide-encoding nucleic acids optimized for selected expression systems (Holler et al. (1993) Gene 136, 323–328; Martin et al. (1995) Gene 154, 150–166) or used to generate degenerate oligonucleotide primers and probes for use in the isolation of natural IKK-α-encoding nucleic acid sequences ("GCG" software, Genetics Computer Group, Inc, Madison Wis.). IKK-α-encoding nucleic acids used in IKK-α-expression vectors and incorporated into recombinant host cells, e.g. for expression and screening, transgenic animals, e.g. for functional studies such as the efficacy of candidate drugs for disease associated with IKK-α-modulated cell function, etc.

The invention also provides nucleic acid hybridization probes and replication/amplification primers having a IKK-α cDNA specific sequence comprising at least 12, preferably at least 24, more preferably at least 36 and most preferably at least contiguous 96 bases of a strand of SEQ ID NO:3, particularly of SEQ ID NO:2, nucleotides 1–1913, and preferably including at least one of bases 1–92, 1811, 1812, 1992, 1995, 2034, 2035, 2039, 2040, 2050, 2055 and 2060, and sufficient to specifically hybridize with a second nucleic acid comprising the complementary strand of SEQ ID NO:3 in the presence of a third nucleic acid comprising (SEQ ID NO:5). Demonstrating specific hybridization generally requires stringent conditions, for example, hybridizing in a buffer comprising 30% formamide in 5×SSPE (0.18 M NaCl, 0.01 M NaPO$_4$, pH7.7, 0.001 M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C. IKK-α nucleic acids can also be distinguished using alignment algorithms, such as BLASTX (Altschul et al. (1990) Basic Local Alignment Search Tool, J Mol Biol 215, 403–410).

In a particular embodiment, the invention provides IKK-α$A^{1628}$ polynucleotides, comprising at least 18, 24, 36, 48, 72, 148, 356 or 728 consecutive nucleotides of the nucleotide sequence set forth as SEQ ID NO:3, which consecutive polynucleotides comprise the polynucleotide 1628 (A) of SEQ ID NO:3. Exemplary IKK-α$A^{1628}$ polynucleotides and allele specific oligonucleotide probes having IKK-αGlu$^{543}$ binding specificity and distinguishable by hybridization assays from IKKα$G^{1628}$ are shown in Table IV.

TABLE IV

| Exemplary IKK-α$A^{1628}$ polynucleotides having IKK-α$A^{1628}$ binding specificity |
| --- |
| αA1 (SEQ ID NO:3, nucleotides 1611–1628) |
| αA2 (SEQ ID NO:3, nucleotides 1628–1644) |
| αA3 (SEQ ID NO:3, nucleotides 1620–1648) |
| αA4 (SEQ ID NO:3, nucleotides 1612–1648) |
| αA5 (SEQ ID NO:3, nucleotides 1608–1668) |
| αA6 (SEQ ID NO:3, nucleotides 1580–1650) |
| αA7 (SEQ ID NO:3, nucleotides 1596–1636) |
| αA8 (SEQ ID NO:3, nucleotides 1602–1687) |
| αA9 (SEQ ID NO:3, nucleotides 1614–1639) |
| αA10 (SEQ ID NO:3, nucleotides 1621–1753) |
| αA11 (SEQ ID NO:3, nucleotides 1502–1899) |
| αA12 (SEQ ID NO:3, nucleotides 1020–1790) |

The subject nucleic acids are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Recombinant nucleic acids comprising the nucleotide sequence of SEQ ID NO:3, or requisite fragments thereof, contain such sequence or fragment at a terminus, immediately flanked by (i.e. contiguous with) a sequence other than that which it is joined to on a natural chromosome, or flanked by a native flanking region fewer than 10 kb, preferably fewer than 2 kb, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

The subject nucleic acids find a wide variety of applications including use as translatable transcripts, hybridization probes, PCR primers, diagnostic nucleic acids, etc.; use in detecting the presence of IKK-α genes and gene transcripts and in detecting or amplifying nucleic acids encoding additional IKK-α homologs and structural analogs. In diagnosis, IKK-α hybridization probes find use in identifying wild-type and mutant IKK-α alleles in clinical and laboratory samples. Mutant alleles are used to generate allele-specific oligonucleotide (ASO) probes for high-throughput clinical diagnoses. In therapy, therapeutic IKK-α nucleic acids are used to modulate cellular expression or intracellular concentration or availability of active IKK-α.

The invention provides efficient methods of identifying agents, compounds or lead compounds for agents active at the level of a IKK modulatable cellular function. Generally, these screening methods involve assaying for compounds which modulate IKK interaction with a natural IKK binding target, in particular, IKK phosphorylation of IκB-derived substrates, particularly IκB and NIK substrates. A wide variety of assays for binding agents are provided including labeled in vitro protein-protein binding assays, immunoassays, cell based assays, etc. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development.

In vitro binding assays employ a mixture of components including an IKK polypeptide, which may be part of a fusion product with another peptide or polypeptide, e.g. a tag for detection or anchoring, etc. The assay mixtures comprise a natural intracellular IKK binding target. In a particular embodiment, the binding target is a substrate comprising IκB serines 32 and/or 36. Such substrates comprise a IκBα, β or ε peptide including the serine 32 and/or 36 residue and at least 5, preferably at least 10, and more preferably at least 20 naturally occurring immediately flanking residues on each side (e.g. for serine 36 peptides, residues 26–46, 22–42, or 12–32 or 151–171 for IκBα, β or ε-derived substrates, respectively). While native full-length binding targets may be used, it is frequently preferred to use portions (e.g. peptides) thereof so long as the portion provides binding affinity and avidity to the subject IKK polypeptide conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like ATP or ATP analogs (for kinase assays), salts, buffers, neutral proteins, e.g. albumin, detergents, protease inhibitors, nuclease inhibitors, antimicrobial agents, etc. may be used.

The resultant mixture is incubated under conditions whereby, but for the presence of the candidate pharmacological agent, the IKK polypeptide specifically binds the cellular binding target, portion or analog with a reference binding affinity. The mixture components can be added in any order that provides for the requisite bindings and incubations may be performed at any temperature which facilitates optimal binding. Incubation periods are likewise selected for optimal binding but also minimized to facilitate rapid, high-throughput screening.

After incubation, the agent-biased binding between the IKK polypeptide and one or more binding targets is detected by any convenient way. For IKK kinase assays, 'binding' is generally detected by a change in the phosphorylation of a IKK-α substrate. In this embodiment, kinase activity may quantified by the transfer to the substrate of a labeled phosphate, where the label may provide for direct detection as radioactivity, luminescence, optical or electron density, etc. or indirect detection such as an epitope tag, etc. A variety of methods may be used to detect the label depending on the nature of the label and other assay components, e.g. through optical or electron density, radiative emissions, nonradiative energy transfers, etc. or indirectly detected with antibody conjugates, etc.

A difference in the binding affinity of the IKK polypeptide to the target in the absence of the agent as compared with the binding affinity in the presence of the agent indicates that the agent modulates the binding of the IKK polypeptide to the IKK binding target. Analogously, in the cell-based assay also described below, a difference in IKK-α-dependent transcriptional activation in the presence and absence of an agent indicates the agent modulates IKK function. A difference, as used herein, is statistically significant and preferably represents at least a 50%, more preferably at least a 90% difference.

The following experimental section and examples are offered by way of illustration and not by way of limitation.

EXPERIMENTAL

Identification of IKK-α

To investigate the mechanism of NIK-mediated NF-κB activation, we identified proteins that associate directly with NIK by yeast two-hybrid protein interaction cloning (Fields and Song, 1989). An expression vector was generated that encodes NIK fused to the DNA-binding domain of the yeast transcription factor GAL4. This vector was used as bait in a two-hybrid screen of a human B cell cDNA library. From approximately six million transformants, eight positive clones were obtained, as determined by activation of his and lacZ reporter genes. Of these clones, three encoded a member of the TRAF family, TRAF3 (Hu et al., 1994; Cheng et al., 1995; Mosialos et al., 1995; Sato et al., 1995) and one encoded a novel protein we call IKK-α. Retransformation into yeast cells verified the interaction between NIK and IKK-α. A full-length human IKK-α clone was isolated by screening a Jurkat cDNA library with a probe generated from the 5'-end of the IKK-α two-hybrid clone. IKK-α comprises an N-terminal serine-threonine kinase catalytic domain, a C-terminal helix-loop-helix domain and a leucine zipper-like amphipathic a-helix juxtaposed in between the helix-loop-helix and kinase domain.

Interaction of IKK-α and NIK in Human Cells

The interaction of IKK-α with NIK was confirmed in mammalian cell coimmunoprecipitation assays. Human IKK-α containing an N-terminal Flag epitope tag was transiently coexpressed in 293 human embryonic kidney cells with Myc epitope-tagged NIK or HA epitope-tagged TRAF proteins. Cell lysates were immunoprecipitated using a monoclonal antibody against the Flag epitope, and coprecipitating NIK or TRAF proteins were detected by immunoblot analysis with an anti-Myc or anti-HA monoclonal antibodies. In this assay, IKK-α was able to coprecipitate NIK confirming the interaction between both proteins as detected for IKK-α by yeast two-hybrid analysis. Also, a deletion mutant IKK-α protein lacking most of the N-terminal kinase domain (IKK-$\alpha_{(307\text{-}745)}$) was able to associate with NIK, indicating that the α-helical C-terminal half of IKK-α mediates the interaction with NIK. In contrast to NIK IKK-α failed to associate with either TRAF2 or TRAF3. However, when NIK was coexpressed with IKK-α and TRAF2, strong coprecipitation of TRAF2 with IKK-α was detected, indicating the formation of a ternary complex between IKK-α, NIK and TRAF2.

Effect of IKK-α and IKK-α Mutants on NF-κB Activation

To investigate a possible role for IKK-α in NF-κB activation, we examined if transient overexpression of IKK-α might activate an NF-κB-dependent reporter gene. An E-selectin-luciferase reporter construct (Schindler and Baichwal, 1994) and a IKK-α expression vector were cotransfected into HeLa cells. IKK-α expression activated the reporter gene in a dose-dependent manner, with a maximal induction of luciferase activity of about 6 to 7-fold compared to vector control. Similar results were obtained in 293 cells, where IKK-α overexpression induced reporter gene activity approximately 4-fold. TNF treatment did not stimulate the weak NF-κB-inducing activity of overexpressed IKK-α in reporter gene assays. Thus, IKK-α induces NF-κB activation when overexpressed.

We next determined the effect of overexpression of kinase-inactive IKK-$\alpha_{(307\text{-}745)}$ that still associates with NIK on signal-induced NF-κB activation in reporter gene assays in 293 cells. Overexpression of IKK-$\alpha_{307\text{-}745)}$ blocked TNF- and IL-1-induced reporter gene activation similar to overexpression of NIK$_{(624\text{-}947)}$. IKK-$\alpha_{(307\text{-}745)}$ was also found to inhibited NF-κB-dependent reporter gene activity elicited by overexpression of TRAF2, TRAF6 and NIK. Taken together these results demonstrate that a catalytically inactive IKK-α mutant is a dominant-negative inhibitor of TNF-, IL-1, TRAF- and NIK-induced NF-κB activation. This indicates that IKK-α functions as a common mediator of NF-κB activation by TNF and IL-1 downstream of NIK.

Parenthetical References

Ansieau, S., et al. (1996). Proc. Natl. Acad. Sci. USA 93, 14053–14058.

Baeuerle, P. A., and Henkel, T. (1994). Annu. Rev. Immunol. 12, 141–179.

Beg, A. A., et al. (1993). Mol. Cell. Biol. 13, 3301–3310.

Cao, Z., Henzel, W. J., and Gao, X. (1996a). Science 271, 1128–1131.

Cao, Z., et al. (1996b). Nature 383, 443–446.

Chen, Z., et al. (1995). Genes Dev. 9, 1586–1597.

Cheng, G., et al. (1995). Science 267, 1494–1498.

Connelly, M. A., and Marcu, K. B. (1995). Cell. Mol. Biol. Res. 41, 537–549.

Dinarello, C. A. (1996). Biologic basis for interleukin-1 in disease. Blood 87, 2095–2147.

Fields, S., and Song, O.-k. (1989). Nature 340, 245–246.

Finco, T. S., and Baldwin, A. S. (1995). Immunity 3, 263–272.

Gedrich, R. W., et al. (1996). J. Biol. Chem. 271, 12852–12858.

Hill, C. S., and Treisman, R. (1995). Cell 80, 199–211.

Hsu, H., Shu, H.-B., Pan, M.-P., and Goeddel, D. V. (1996). Cell 84, 299–308.

Hu, H. M., et al. (1994). J. Biol. Chem. 269, 30069–30072.

Lee, S. Y., et al. (1996). Proc. Natl. Acad. Sci. USA 93, 9699–9703.

Lenardo, M., and Baltimore, D. (1989). Cell 58, 227–229.

Malinin, N. L., et al. (1997). Nature 385, 540–544.

Mock et al. (1995). Genomics 27, 348–351.

Mosialos, G., et al. (1995). Cell 80, 389–399.

Nakano, H., et al. (1996). J. Biol. Chem. 271, 14661–14664.

Osborn, L., Kunkel, S., and Nabel, G. J. (1989). Proc. Natl. Acad. Sci. USA 86, 2336–2340.

Rothe, M., Sarma, V., Dixit, V. M., and Goeddel, D. V. (1995). Science 269, 1424–1427.

Rothe, M., Wong, S. C., Henzel, W. J., and Goeddel, D. V. (1994). Cell 78, 681–692.

Sato, T., Irie, S., and Reed, J. C. (1995). FEBS Lett. 358, 113–118.

Schindler, U., and Baichwal, V. R. (1994). Mol. Cell. Biol. 14, 5820–5831.

Smith, C. A., Farrah, T., and Goodwin, R. G. (1994). Cell 76, 959–962.

Song, H. Y., and Donner, D. B. (1995). Biochem. J. 809, 825–829.

Thanos, D., and Maniatis, T. (1995). Cell 80, 529–532.

Verma, I. M., et al. (1995). Genes Dev. 9, 2723–2735.

EXAMPLES

1. Protocol for at IKK-α-IκBα Phosphorylation Assay.

A. Reagents:

Neutralite Avidin: 20 μg/ml in PBS.

kinase: $10^{-8}$–$10^{-5}$ M IKK-α (SEQ ID NO:4) at 20 μg/ml in PBS.

substrate: $10^{-7}$–$10^{-4}$ M biotinylated substrate (21 residue peptide consisting of residues 26–46 of human IκBα) at 40 μg/ml in PBS.

Blocking buffer: 5% BSA, 0.5% Tween 20 in PBS; 1 hour at room temperature.

Assay Buffer: 100 mM KCl, 10 mM $MgCl_2$, 1 mM $MnCl_2$, 20 mM HEPES pH 7.4, 0.25 mM EDTA, 1% glycerol, 0.5% NP-40, 50 mM BME, 1 mg/ml BSA, cocktail of protease inhibitors.

[$^{32}$P]γ-ATP 10× stock: $2\times10^{-5}$ M cold ATP with 100 μCi [$^{32}$P]γ-ATP. Place in the 4° C. microfridge during screening.

Protease inhibitor cocktail (1000×): 10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB # 917575), and 2 mM $NaVo_3$ (Sigma # S-6508) in 10 ml of PBS.

B. Preparation of Assay Plates:

Coat with 120 μl of stock N Avidin per well overnight at 4° C.

Wash 2 times with 200 μl PBS.

Block with 150 μl of blocking buffer.

Wash 2 times with 200 μl PBS.

C. Assay:

Add 40 μl assay buffer/well.

Add 40 μl biotinylated substrate (2–200 pmoles/40 ul in assay buffer)

Add 40 μl kinase (0.1–10 pmoles/40 ul in assay buffer)

Add 10 μl compound or extract.

Add 10 μl [$^{32}$P]γ-ATP 10× stock.

Shake at 25° C. for 15 minutes.

Incubate additional 45 minutes at 25° C.

Stop the reaction by washing 4 times with 200 μl PBS.

Add 150 μl scintillation cocktail.

Count in Topcount.

D. Controls for all assays (located on each plate):

a. Non-specific binding b. cold ATP at 80% inhibition.

2. Protocol for high throughput IKK-α-NIK binding assay.

A. Reagents:

Neutralite Avidin: 20 μg/ml in PBS.

Blocking buffer: 5% BSA, 0.5% Tween 20 in PBS; 1 hour at room temperature.

Assay Buffer: 100 mM KCl, 20 mM HEPES pH 7.6, 1 mM $MgCl_2$, 1% glycerol, 0.5% NP-40, 50 mM β-mercaptoethanol, 1 mg/ml BSA, cocktail of protease inhibitors.

$^{33}$P IKK-α polypeptide 10× stock: $10^{-8}$–$10^{-6}$ M "cold" IKK-α supplemented with 200,000–250,000 cpm of labeled IKK-α (Beckman counter). Place in the 4° C. microfridge during screening.

Protease inhibitor cocktail (1000×): 10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB # 917575), and 2mM $NaVO_3$ (Sigma # S-6508) in 10 ml of PBS.

NIK: $10^{-7}$–$10^{-5}$ M biotinylated NIK in PBS.

B. Preparation of assay plates:

Coat with 120 μl of stock N-Avidin per well overnight at 4° C.

Wash 2 times with 200 μl PBS.

Block with 150 μl of blocking buffer.

Wash 2 times with 200 μl PBS.

C. Assay:

Add 40 μl assay buffer/well.

Add 10 μl compound or extract.

Add 10 μl $^{33}$P-IKK-α (20–25,000 cpm/0.1–10 pmoles/well=$10^{-9}$–$10^{-7}$ M final conc).

Shake at 25° C. for 15 minutes.

Incubate additional 45 minutes at 25° C.

Add 40 μM biotinylated NIK (0.1–10 pmoles/40 ul in assay buffer)

Incubate 1 hour at room temperature.

Stop the reaction by washing 4 times with 200 μM PBS.

Add 150 μM scintillation cocktail.

Count in Topcount.

D. Controls for all assays (located on each plate):

a. Non-specific binding b. Soluble (non-biotinylated NIK) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

---

What is claimed is:

1. An isolated polypeptide comprising at least 10 consecutive residues of the amino acid sequence set forth as SEQ ID NO:4, which consecutive amino acid residues comprise (a) at least one of the amino acid residues 679, 680, 684, 686 and 687 of SEQ ID NO:4 and (b) the amino acid residue 543 (Glu) of SEQ ID NO:4.

2. An isolated polypeptide according to claim 1, wherein said polypeptide has an activity selected from at least one of: a kinase or kinase inhibitory activity, a NIK-binding or binding inhibitory activity, an IκB-binding or binding inhibitory activity and an NFκB activating or inhibitory activity.

3. An isolated polypeptide according to claim 1, wherein the consecutive amino acid residues comprise the amino acid residue 679 of SEQ ID NO:4.

4. An isolated polypeptide according to claim 1, wherein the consecutive amino acid residues comprise the amino acid residue 680 of SEQ ID NO:4.

5. An isolated polypeptide according to claim 1, wherein the consecutive amino acid residues comprise the amino acid residue 684 of SEQ ID NO:4.

6. An isolated polypeptide according to claim 1, wherein the consecutive amino acid residues comprise the amino acid residue 686 of SEQ ID NO:4.

7. An isolated polypeptide according to claim 1, wherein the consecutive amino acid residues comprise the amino acid residue 687 of SEQ ID NO:4.

8. An isolated polypeptide according to claim 1, wherein the consecutive amino acid residues comprise the amino acid residues 540–548 of SEQ ID NO:4.

9. An isolated polypeptide according to claim 1, wherein the consecutive amino acid residues comprise the amino acid residues 543–550 of SEQ ID NO:4.

10. An isolated polypeptide according to claim 1, wherein the consecutive amino acid residues comprise the amino acid residues 536–543 of SEQ ID NO:4.

11. An isolated polypeptide according to claim 1, wherein the consecutive amino acid residues comprise the amino acid residues 534–554 of SEQ ID NO:4.

12. An isolated polypeptide according to claim 1, wherein the consecutive amino acid residues comprise the amino acid residues 533–543 of SEQ ID NO:4.

13. An isolated polypeptide according to claim 1, wherein the consecutive ammo acid residues comprise the amino acid residues 543–563 of SEQ ID NO:4.

14. An isolated polypeptide according to claim 1, wherein the consecutive amino acid residues comprise the amino acid residues 542–549 of SEQ ID NO:4.

15. An isolated polypeptide according to claim 1, wherein the consecutive amino acid residues comprise the amino acid residues 538–545 of SEQ ID NO:4.

16. An isolated polypeptide according to claim 1, wherein the consecutive amino acid residues comprise the amino acid residues 541–547 of SEQ ID NO:4.

17. An isolated polypeptide according to claim 1, wherein the consecutive amino acid residues comprise an amino acid sequence selected from residues 403–543 and 543–604 of SEQ ID NO:4.

18. A method of screening for an agent which modulates the interaction of an IKK polypeptide to a binding target, said method comprising the steps of:

incubating a mixture comprising:
an isolated polypeptide according to claim 1,
a binding target of said polypeptide, and
a candidate agent;
under conditions whereby, but for the presence of said agent, said polypeptide specifically binds said binding target at a reference affinity;
detecting the binding affinity of said polypeptide to said binding target to determine an agent-biased affinity, wherein a difference between the agent-biased affinity and the reference affinity indicates that said agent modulates the binding of said polypeptide to said binding target.

19. A method according to claim 18, wherein said binding target is a natural intracellular substrate and said reference and agent-biased binding affinity is detected as phosphorylation of said substrate.

20. A method of screening for an agent which modulates the ability of an IKK polypeptide to specifically phosphorylate an IκB polypeptide, said method comprising the steps of:

incubating a mixture comprising: an isolated polypeptide according to claim 1 retaining IκB kinase activity, an IκB polypeptide comprising at least a six residue domain of a natural IκB comprising at least one of Ser32 and Ser36, and a candidate agent;
under conditions whereby, but for the presence of said agent, said polypeptide specifically phosphorylates said IκB polypeptide at at least one of said Ser32 and Ser36 at a reference activity; detecting the polypeptide-induced phosphorylation of said IκB polypeptide at at least one of said Ser32 and Ser36 to determine an agent-biased activity, wherein a difference between the agent-biased activity and the reference activity indicates that said agent modulates the ability of said polypeptide to specifically phosphorylate an IκB polypeptide.

* * * * *

UNITED STATES PATENT AND TRADEMARK OFFICE
CERTIFICATE OF CORRECTION

PATENT NO.   : 6,479,266 B2　　　　　　　　　　　　　　　　　　　　　　　Page 1 of 1
DATED        : June 15, 2004
INVENTOR(S)  : John Williamson It is certified that error appears in the above-identified patent and that said Letters Patent is hereby corrected as shown below:

Column 9,
Line 67, after "on", please delete "respective".

Signed and Sealed this

Seventeenth Day of August, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,479,266 B1
DATED : November 12, 2002
INVENTOR(S) : Mike Rothe et al.

It is certified that error appears in the above-identified patent and that said Letters Patent is hereby corrected as shown below:

This certificate supersedes Certificate of Correction issued August 17, 2004, the number was erroneously mentioned and should be vacated since no Certificate of Correction was granted.

Signed and Sealed this

Fourteenth Day of June, 2005

JON W. DUDAS
*Director of the United States Patent and Trademark Office*

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 2268 base pairs (B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO:1:

```
ATGAGCTGGT CACCTTCCCT GACAACGCAG ACATGTGGGG CCTGGGAAAT GAAAGAGCGC      60
CTTGGGACAG GGGGATTTGG AAATGTCATC CGATGGCACA ATCAGGAAAC AGGTGAGCAG     120
ATTGCCATCA AGCAGTGCCG GCAGGAGCTC AGCCCCCGGA ACCGAGAGCG GTGGTGCCTG     180
GAGATCCAGA TCATGAGAAG GCTGACCCAC CCCAATGTGG TGGCTGCCCG AGATGTCCCT     240
GAGGGGATGC AGAACTTGGC GCCCAATGAC CTGCCCCTGC TGGCCATGGA GTACTGCCAA     300
GGAGGAGATC TCCGGAAGTA CCTGAACCAG TTTGAGAACT GCTGTGGTCT GCGGGAAGGT     360
GCCATCCTCA CCTTGCTGAG TGACATTGCC TCTGCGCTTA GATACCTTCA TGAAAACAGA     420
ATCATCCATC GGGATCTAAA GCCAGAAAAC ATCGTCCTGC AGCAAGGAGA ACAGAGGTTA     480
ATACACAAAA TTATTGACCT AGGATATGCC AAGGAGCTGG ATCAGGGCAG TCTTTGCACA     540
TCATTCGTGG GGACCCTGCA GTACCTGGCC CCAGAGCTAC TGGAGCAGCA GAAGTACACA     600
GTGACCGTCG ACTACTGGAG CTTCGGCACC CTGGCCTTTG AGTGCATCAC GGGCTTCCGG     660
CCCTTCCTCC CCAACTGGCA GCCCGTGCAG TGGCATTCAA AAGTGCGGCA GAAGAGTGAG     720
GTGGACATTG TTGTTAGCGA AGACTTGAAT GGAACGGTGA AGTTTTCAAG CTCTTTACCC     780
TACCCCAATA ATCTTAACAG TGTCCTGGCT GAGCGACTGG AGAAGTGGCT GCAACTGATG     840
CTGATGTGGC ACCCCCGACA GAGGGGCACG GATCCCACGT ATGGGCCCAA TGGCTGCTTC     900
AAGGCCCTGG ATGACATCTT AAACTTAAAG CTGGTTCATA TCTTGAACAT GGTCACGGGC     960
ACCATCCACA CCTACCCTGT GACAGAGGAT GAGAGTCTGC AGAGCTTGAA GGCCAGAATC    1020
CAACAGGACA CGGGCATCCC AGAGGAGGAC CAGGAGCTGC TGCAGGAAGC GGGCCTGGCG    1080
TTGATCCCCG ATAAGCCTGC CACTCAGTGT ATTTCAGACG GCAAGTTAAA TGAGGGCCAC    1140
ACATTGGACA TGGATCTTGT TTTTCTCTTT GACAACAGTA AAATCACCTA TGAGACTCAG    1200
ATCTCCCCAC GGCCCCAACC TGAAAGTGTC AGCTGTATCC TTCAAGAGCC AAGAGGAAT    1260
CTCGCCTTCT TCCAGCTGAG GAAGGTGTGG GGCCAGGTCT GGCACAGCAT CCAGACCCTG    1320
AAGGAAGATT GCAACCGGCT GCAGCAGGGA CAGCGAGCCG CCATGATGAA TCTCCTCCGA    1380
AACAACAGCT GCCTCTCCAA AATGAAGAAT TCCATGGCTT CCATGTCTCA GCAGCTCAAG    1440
GCCAAGTTGG ATTTCTTCAA AACCAGCATC CAGATTGACC TGGAGAAGTA CAGCGAGCAA    1500
ACCGAGTTTG GGATCACATC AGATAAACTG CTGCTGGCCT GGAGGGAAAT GGAGCAGGCT    1560
GTGGAGCTCT GTGGGCGGGA GAACGAAGTG AAACTCCTGG TAGAACGGAT GATGGCTCTG    1620
CAGACCGACA TTGTGGACTT ACAGAGGAGC CCCATGGGCC GGAAGCAGGG GGGAACGCTG    1680
GACGACCTAG AGGAGCAAGC AAGGGAGCTG TACAGGAGAC TAAGGGAAAA ACCTCGAGAC    1740
CAGCGAACTG AGGGTGACAG TCAGGAAATG GTACGGCTGC TGCTTCAGGC AATTCAGAGC    1800
TTCGAGAAGA AAGTGCGAGT GATCTATACG CAGCTCAGTA AAACTGTGGT TGCAAGCAG    1860
AAGGCGCTGG AACTGTTGCC AAGGTGGAA GAGGTGGTGA GCTTAATGAA TGAGGATGAG    1920
AAGACTGTTG TCCGGCTGCA GGAGAAGCGG CAGAAGGAGC TCTGGAATCT CCTGAAGATT    1980
GCTTGTAGCA AGGTCCGTGG TCCTGTCAGT GGAAGCCCGG ATAGCATGAA TGCCTCTCGA    2040
CTTAGCCAGC CTGGGCAGCT GATGTCTCAG CCCTCCACGG CCTCCAACAG CTTACCTGAG    2100
CCAGCCAAGA AGAGTGAAGA ACTGGTGGCT GAAGCACATA ACCTCTGCAC CCTGCTAGAA    2160
```

```
AATGCCATAC AGGACACTGT GAGGGAACAA GACCAGAGTT TCACGGCCCT AGACTGGAGC    2220

TGGTTACAGA CGGAAGAAGA AGAGCACAGC TGCCTGGAGC AGGCCTCA                2268
```

(2) INFORMATION FOR SEQ ID NO:2:

(i) SEQUENCE CHARACTERISTICS:
        (A) LENGTH: 756 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Met Ser Trp Ser Pro Ser Leu Thr Thr Gln Thr Cys Gly Ala Trp Glu
 1               5                  10                  15

Met Lys Glu Arg Leu Gly Thr Gly Gly Phe Gly Asn Val Ile Arg Trp
                20                  25                  30

His Asn Gln Glu Thr Gly Glu Gln Ile Ala Ile Lys Gln Cys Arg Gln
            35                  40                  45

Glu Leu Ser Pro Arg Asn Arg Glu Arg Trp Cys Leu Glu Ile Gln Ile
        50                  55                  60

Met Arg Arg Leu Thr His Pro Asn Val Val Ala Ala Arg Asp Val Pro
65                  70                  75                  80

Glu Gly Met Gln Asn Leu Ala Pro Asn Asp Leu Pro Leu Leu Ala Met
                85                  90                  95

Glu Tyr Cys Gln Gly Gly Asp Leu Arg Lys Tyr Leu Asn Gln Phe Glu
            100                 105                 110

Asn Cys Cys Gly Leu Arg Glu Gly Ala Ile Leu Thr Leu Leu Ser Asp
        115                 120                 125

Ile Ala Ser Ala Leu Arg Tyr Leu His Glu Asn Arg Ile Ile His Arg
    130                 135                 140

Asp Leu Lys Pro Glu Asn Ile Val Leu Gln Gln Gly Glu Gln Arg Leu
145                 150                 155                 160

Ile His Lys Ile Ile Asp Leu Gly Tyr Ala Lys Glu Leu Asp Gln Gly
                165                 170                 175

Ser Leu Cys Thr Ser Phe Val Gly Thr Leu Gln Tyr Leu Ala Pro Glu
            180                 185                 190

Leu Leu Glu Gln Gln Lys Tyr Thr Val Thr Val Asp Tyr Trp Ser Phe
        195                 200                 205

Gly Thr Leu Ala Phe Glu Cys Ile Thr Gly Phe Arg Pro Phe Leu Pro
    210                 215                 220

Asn Trp Gln Pro Val Gln Trp His Ser Lys Val Arg Gln Lys Ser Glu
225                 230                 235                 240

Val Asp Ile Val Val Ser Glu Asp Leu Asn Gly Thr Val Lys Phe Ser
                245                 250                 255

Ser Ser Leu Pro Tyr Pro Asn Asn Leu Asn Ser Val Leu Ala Glu Arg
            260                 265                 270

Leu Glu Lys Trp Leu Gln Leu Met Leu Met Trp His Pro Arg Gln Arg
        275                 280                 285

Gly Thr Asp Pro Thr Tyr Gly Pro Asn Gly Cys Phe Lys Ala Leu Asp
    290                 295                 300

Asp Ile Leu Asn Leu Lys Leu Val His Ile Leu Asn Met Val Thr Gly
305                 310                 315                 320

Thr Ile His Thr Tyr Pro Val Thr Glu Asp Glu Ser Leu Gln Ser Leu
```

```
                    325                 330                 335
Lys Ala Arg Ile Gln Gln Asp Thr Gly Ile Pro Glu Asp Gln Glu
                340                 345                 350
Leu Leu Gln Glu Ala Gly Leu Ala Leu Ile Pro Asp Lys Pro Ala Thr
                355                 360                 365
Gln Cys Ile Ser Asp Gly Lys Leu Asn Glu Gly His Thr Leu Asp Met
    370                 375                 380
Asp Leu Val Phe Leu Phe Asp Asn Ser Lys Ile Thr Tyr Glu Thr Gln
385                 390                 395                 400
Ile Ser Pro Arg Pro Gln Pro Glu Ser Val Ser Cys Ile Leu Gln Glu
                405                 410                 415
Pro Lys Arg Asn Leu Ala Phe Phe Gln Leu Arg Lys Val Trp Gly Gln
                420                 425                 430
Val Trp His Ser Ile Gln Thr Leu Lys Glu Asp Cys Asn Arg Leu Gln
        435                 440                 445
Gln Gly Gln Arg Ala Ala Met Met Asn Leu Leu Arg Asn Asn Ser Cys
    450                 455                 460
Leu Ser Lys Met Lys Asn Ser Met Ala Ser Met Ser Gln Gln Leu Lys
465                 470                 475                 480
Ala Lys Leu Asp Phe Phe Lys Thr Ser Ile Gln Ile Asp Leu Glu Lys
                485                 490                 495
Tyr Ser Glu Gln Thr Glu Phe Gly Ile Thr Ser Asp Lys Leu Leu Leu
                500                 505                 510
Ala Trp Arg Glu Met Glu Gln Ala Val Glu Leu Cys Gly Arg Glu Asn
                515                 520                 525
Glu Val Lys Leu Leu Val Glu Arg Met Met Ala Leu Gln Thr Asp Ile
            530                 535                 540
Val Asp Leu Gln Arg Ser Pro Met Gly Arg Lys Gln Gly Gly Thr Leu
545                 550                 555                 560
Asp Asp Leu Glu Glu Gln Ala Arg Glu Leu Tyr Arg Arg Leu Arg Glu
                565                 570                 575
Lys Pro Arg Asp Gln Arg Thr Glu Gly Asp Ser Gln Glu Met Val Arg
            580                 585                 590
Leu Leu Leu Gln Ala Ile Gln Ser Phe Glu Lys Lys Val Arg Val Ile
        595                 600                 605
Tyr Thr Gln Leu Ser Lys Thr Val Val Cys Lys Gln Lys Ala Leu Glu
    610                 615                 620
Leu Leu Pro Lys Val Glu Val Val Ser Leu Met Asn Glu Asp Glu
625                 630                 635                 640
Lys Thr Val Val Arg Leu Gln Glu Lys Arg Gln Lys Glu Leu Trp Asn
                645                 650                 655
Leu Leu Lys Ile Ala Cys Ser Lys Val Arg Gly Pro Val Ser Gly Ser
            660                 665                 670
Pro Asp Ser Met Asn Ala Ser Arg Leu Ser Gln Pro Gly Gln Leu Met
        675                 680                 685
Ser Gln Pro Ser Thr Ala Ser Asn Ser Leu Pro Glu Pro Ala Lys Lys
    690                 695                 700
Ser Glu Glu Leu Val Ala Glu Ala His Asn Leu Cys Thr Leu Leu Glu
705                 710                 715                 720
Asn Ala Ile Gln Asp Thr Val Arg Glu Gln Asp Gln Ser Phe Thr Ala
                725                 730                 735
Leu Asp Trp Ser Trp Leu Gln Thr Glu Glu Glu His Ser Cys Leu
                740                 745                 750
```

Glu Gln Ala Ser
       755

(2) INFORMATION FOR SEQ ID NO:3:

(i) SEQUENCE CHARACTERISTICS:
        (A) LENGTH: 2238 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

| | | | | | |
|---|---|---|---|---|---|
| ATGGAGCGGC | CCCCGGGGCT | GCGGCCGGGC | GCGGGCGGGC | CCTGGGAGAT | GCGGGAGCGG | 60 |
| CTGGGCACCG | GCGGCTTCGG | GAACGTCTGT | CTGTACCAGC | ATCGGGAACT | TGATCTCAAA | 120 |
| ATAGCAATTA | AGTCTTGTCG | CCTAGAGCTA | AGTACCAAAA | ACAGAGAACG | ATGGTGCCAT | 180 |
| GAAATCCAGA | TTATGAAGAA | GTTGAACCAT | GCCAATGTTG | TAAAGGCCTG | TGATGTTCCT | 240 |
| GAAGAATTGA | ATATTTTGAT | TCATGATGTG | CCTCTTCTAG | CAATGGAATA | CTGTTCTGGA | 300 |
| GGAGATCTCC | GAAAGCTGCT | CAACAAACCA | GAAAATTGTT | GTGGACTTAA | AGAAAGCCAG | 360 |
| ATACTTTCTT | TACTAAGTGA | TATAGGGTCT | GGGATTCGAT | ATTTGCATGA | AAACAAAATT | 420 |
| ATACATCGAG | ATCTAAAACC | TGAAAACATA | GTTCTTCAGG | ATGTTGGTGG | AAAGATAATA | 480 |
| CATAAAATAA | TTGATCTGGG | ATATGCCAAA | GATGTTGATC | AAGGAAGTCT | GTGTACATCT | 540 |
| TTTGTGGGAA | CACTGCAGTA | TCTGGCCCCA | GAGCTCTTTG | AGAATAAGCC | TTACACAGCC | 600 |
| ACTGTTGATT | ATTGGAGCTT | TGGGACCATG | GTATTTGAAT | GTATTGCTGG | ATATAGGCCT | 660 |
| TTTTTGCATC | ATCTGCAGCC | ATTTACCTGG | CATGAGAAGA | TTAAGAAGAA | GGATCCAAAG | 720 |
| TGTATATTTG | CATGTGAAGA | GATGTCAGGA | GAAGTTCGGT | TTAGTAGCCA | TTTACCTCAA | 780 |
| CCAAATAGCC | TTTGTAGTTT | AATAGTAGAA | CCCATGGAAA | ACTGGCTACA | GTTGATGTTG | 840 |
| AATTGGGACC | CTCAGCAGAG | AGGAGGACCT | GTTGACCTTA | CTTTGAAGCA | GCCAAGATGT | 900 |
| TTTGTATTAA | TGGATCACAT | TTTGAATTTG | AAGATAGTAC | ACATCCTAAA | TATGACTTCT | 960 |
| GCAAAGATAA | TTTCTTTTCT | GTTACCACCT | GATGAAAGTC | TTCATTCACT | ACAGTCTCGT | 1020 |
| ATTGAGCGTG | AAACTGGAAT | AAATACTGGT | TCTCAAGAAC | TTCTTTCAGA | GACAGGAATT | 1080 |
| TCTCTGGATC | CTCGGAAACC | AGCCTCTCAA | TGTGTTCTAG | ATGGAGTTAG | AGGCTGTGAT | 1140 |
| AGCTATATGG | TTTATTTGTT | TGATAAAAGT | AAAACTGTAT | ATGAAGGGCC | ATTTGCTTCC | 1200 |
| AGAAGTTTAT | CTGATTGTGT | AAATTATATT | GTACAGGACA | GCAAAATACA | GCTTCCAATT | 1260 |
| ATACAGCTGC | GTAAAGTGTG | GGCTGAAGCA | GTGCACTATG | TGTCTGGACT | AAAAGAAGAC | 1320 |
| TATAGCAGGC | TCTTTCAGGG | ACAAAGGGCA | GCAATGTTAA | GTCTTCTTAG | ATATAATGCT | 1380 |
| AACTTAACAA | AAATGAAGAA | CACTTTGATC | TCAGCATCAC | AACAACTGAA | AGCTAAATTG | 1440 |
| GAGTTTTTTC | ACAAAAGCAT | TCAGCTTGAC | TTGGAGAGAT | ACAGCGAGCA | GATGACGTAT | 1500 |
| GGGATATCTT | CAGAAAAAAT | GCTAAAAGCA | TGGAAAGAAA | TGGAAGAAAA | GGCCATCCAC | 1560 |
| TATGCTGAGG | TTGGTGTCAT | TGGATACCTG | GAGGATCAGA | TTATGTCTTT | GCATGCTGAA | 1620 |
| ATCATGGAGC | TACAGAAGAG | CCCCTATGGA | AGACGTCAGG | GAGACTTGAT | GGAATCTCTG | 1680 |
| GAACAGCGTG | CCATTGATCT | ATATAAGCAG | TTAAAACACA | GACCTTCAGA | TCACTCCTAC | 1740 |
| AGTGACAGCA | CAGAGATGGT | GAAAATCATT | GTGCACACTG | TGCAGAGTCA | GGACCGTGTG | 1800 |
| CTCAAGGAGC | TGTTTGGTCA | TTTGAGCAAG | TTGTTGGGCT | GTAAGCAGAA | GATTATTGAT | 1860 |

```
CTACTCCCTA AGGTGGAAGT GGCCCTCAGT AATATCAAAG AAGCTGACAA TACTGTCATG    1920

TTCATGCAGG GAAAAAGGCA GAAAGAAATA TGGCATCTCC TTAAAATTGC CTGTACACAG    1980

AGTTCTGCCC GGTCCCTTGT AGGATCCAGT CTAGAAGGTG CAGTAACCCC TCAGACATCA    2040

GCATGGCTGC CCCCGACTTC AGCAGAACAT GATCATTCTC TGTCATGTGT GGTAACTCCT    2100

CAAGATGGGG AGACTTCAGC ACAAATGATA GAAGAAAATT TGAACTGCCT TGGCCATTTA    2160

AGCACTATTA TTCATGAGGC AAATGAGGAA CAGGGCAATA GTATGATGAA TCTTGATTGG    2220

AGTTGGTTAA CAGAATGA                                                  2238
```

(2) INFORMATION FOR SEQ ID NO:4:

(i) SEQUENCE CHARACTERISTICS:
        (A) LENGTH: 745 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Met Glu Arg Pro Pro Gly Leu Arg Pro Gly Ala Gly Pro Trp Glu
 1               5                  10                  15

Met Arg Glu Arg Leu Gly Thr Gly Gly Phe Gly Asn Val Cys Leu Tyr
                20                  25                  30

Gln His Arg Glu Leu Asp Leu Lys Ile Ala Ile Lys Ser Cys Arg Leu
        35                  40                  45

Glu Leu Ser Thr Lys Asn Arg Glu Arg Trp Cys His Glu Ile Gln Ile
    50                  55                  60

Met Lys Lys Leu Asn His Ala Asn Val Val Lys Ala Cys Asp Val Pro
65                  70                  75                  80

Glu Glu Leu Asn Ile Leu Ile His Asp Val Pro Leu Leu Ala Met Glu
                85                  90                  95

Tyr Cys Ser Gly Gly Asp Leu Arg Lys Leu Leu Asn Lys Pro Glu Asn
                100                 105                 110

Cys Cys Gly Leu Lys Glu Ser Gln Ile Leu Ser Leu Leu Ser Asp Ile
        115                 120                 125

Gly Ser Gly Ile Arg Tyr Leu His Glu Asn Lys Ile Ile His Arg Asp
    130                 135                 140

Leu Lys Pro Glu Asn Ile Val Leu Gln Asp Val Gly Gly Lys Ile Ile
145                 150                 155                 160

His Lys Ile Ile Asp Leu Gly Tyr Ala Lys Asp Val Asp Gln Gly Ser
                165                 170                 175

Leu Cys Thr Ser Phe Val Gly Thr Leu Gln Tyr Leu Ala Pro Glu Leu
                180                 185                 190

Phe Glu Asn Lys Pro Tyr Thr Ala Thr Val Asp Tyr Trp Ser Phe Gly
        195                 200                 205

Thr Met Val Phe Glu Cys Ile Ala Gly Tyr Arg Pro Phe Leu His His
    210                 215                 220

Leu Gln Pro Phe Thr Trp His Glu Lys Ile Lys Lys Lys Asp Pro Lys
225                 230                 235                 240

Cys Ile Phe Ala Cys Glu Glu Met Ser Gly Glu Val Arg Phe Ser Ser
                245                 250                 255

His Leu Pro Gln Pro Asn Ser Leu Cys Ser Leu Ile Val Glu Pro Met
                260                 265                 270

Glu Asn Trp Leu Gln Leu Met Leu Asn Trp Asp Pro Gln Gln Arg Gly
```

-continued

```
            275                 280                 285
Gly Pro Val Asp Leu Thr Leu Lys Gln Pro Arg Cys Phe Val Leu Met
    290                 295                 300
Asp His Ile Leu Asn Leu Lys Ile Val His Ile Leu Asn Met Thr Ser
305                 310                 315                 320
Ala Lys Ile Ile Ser Phe Leu Leu Pro Pro Asp Glu Ser Leu His Ser
                325                 330                 335
Leu Gln Ser Arg Ile Glu Arg Glu Thr Gly Ile Asn Thr Gly Ser Gln
                340                 345                 350
Glu Leu Leu Ser Glu Thr Gly Ile Ser Leu Asp Pro Arg Lys Pro Ala
                355                 360                 365
Ser Gln Cys Val Leu Asp Gly Val Arg Gly Cys Asp Ser Tyr Met Val
    370                 375                 380
Tyr Leu Phe Asp Lys Ser Lys Thr Val Tyr Glu Gly Pro Phe Ala Ser
385                 390                 395                 400
Arg Ser Leu Ser Asp Cys Val Asn Tyr Ile Val Gln Asp Ser Lys Ile
                405                 410                 415
Gln Leu Pro Ile Ile Gln Leu Arg Lys Val Trp Ala Glu Ala Val His
                420                 425                 430
Tyr Val Ser Gly Leu Lys Glu Asp Tyr Ser Arg Leu Phe Gln Gly Gln
                435                 440                 445
Arg Ala Ala Met Leu Ser Leu Leu Arg Tyr Asn Ala Asn Leu Thr Lys
    450                 455                 460
Met Lys Asn Thr Leu Ile Ser Ala Ser Gln Gln Leu Lys Ala Lys Leu
465                 470                 475                 480
Glu Phe Phe His Lys Ser Ile Gln Leu Asp Leu Glu Arg Tyr Ser Glu
                485                 490                 495
Gln Met Thr Tyr Gly Ile Ser Ser Glu Lys Met Leu Lys Ala Trp Lys
                500                 505                 510
Glu Met Glu Glu Lys Ala Ile His Tyr Ala Glu Val Gly Val Ile Gly
                515                 520                 525
Tyr Leu Glu Asp Gln Ile Met Ser Leu His Ala Glu Ile Met Glu Leu
    530                 535                 540
Gln Lys Ser Pro Tyr Gly Arg Arg Gln Gly Asp Leu Met Glu Ser Leu
545                 550                 555                 560
Glu Gln Arg Ala Ile Asp Leu Tyr Lys Gln Leu Lys His Arg Pro Ser
                565                 570                 575
Asp His Ser Tyr Ser Asp Ser Thr Glu Met Val Lys Ile Ile Val His
                580                 585                 590
Thr Val Gln Ser Gln Asp Arg Val Leu Lys Glu Leu Phe Gly His Leu
    595                 600                 605
Ser Lys Leu Leu Gly Cys Lys Gln Lys Ile Ile Asp Leu Leu Pro Lys
    610                 615                 620
Val Glu Val Ala Leu Ser Asn Ile Lys Glu Ala Asp Asn Thr Val Met
625                 630                 635                 640
Phe Met Gln Gly Lys Arg Gln Lys Glu Ile Trp His Leu Leu Lys Ile
                645                 650                 655
Ala Cys Thr Gln Ser Ser Ala Arg Ser Leu Val Gly Ser Ser Leu Glu
                660                 665                 670
Gly Ala Val Thr Pro Gln Thr Ser Ala Trp Leu Pro Pro Thr Ser Ala
                675                 680                 685
Glu His Asp His Ser Leu Ser Cys Val Val Thr Pro Gln Asp Gly Glu
    690                 695                 700
```

```
Thr Ser Ala Gln Met Ile Glu Glu Asn Leu Asn Cys Leu Gly His Leu
705                 710                 715                 720

Ser Thr Ile Ile His Glu Ala Asn Glu Glu Gln Gly Asn Ser Met Met
            725                 730                 735

Asn Leu Asp Trp Ser Trp Leu Thr Glu
            740                 745

(2) INFORMATION FOR SEQ ID NO:5:

(i) SEQUENCE CHARACTERISTICS:
        (A) LENGTH: 2146 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:5:

GTACCAGCAT CGGGAACTTG ATCTCAAAAT AGCAATTAAG TCTTGTCGCC TAGAGCTAAG       60

TACCAAAAAC AGAGAACGAT GGTGCCATGA AATCCAGATT ATGAAGAAGT TGAACCATGC      120

CAATGTTGTA AAGGCCTGTG ATGTTCCTGA AGAATTGAAT ATTTTGATTC ATGATGTGCC      180

TCTTCTAGCA ATGGAATACT GTTCTGGAGG AGATCTCCGA AAGCTGCTCA ACAAACCAGA      240

AAATTGTTGT GGACTTAAAG AAAGCCAGAT ACTTTCTTTA CTAAGTGATA TAGGGTCTGG      300

GATTCGATAT TTGCATGAAA ACAAAATTAT ACATCGAGAT CTAAAACCTG AAAACATAGT      360

TCTTCAGGAT GTTGGTGGAA AGATAATACA TAAAATAATT GATCTGGGAT ATGCCAAAGA      420

TGTTGATCAA GGAAGTCTGT GTACATCTTT TGTGGGAACA CTGCAGTATC TGGCCCCAGA      480

GCTCTTTGAG AATAAGCCTT ACACAGCCAC TGTTGATTAT TGGAGCTTTG GACCATGGT      540

ATTTGAATGT ATTGCTGGAT ATAGGCCTTT TTTGCATCAT CTGCAGCCAT TTACCTGGCA      600

TGAGAAGATT AAGAAGAAGG ATCCAAAGTG TATATTTGCA TGTGAAGAGA TGTCAGGAGA      660

AGTTCGGTTT AGTAGCCATT TACCTCAACC AAATAGCCTT TGTAGTTTAA TAGTAGAACC      720

CATGGAAAAC TGGCTACAGT TGATGTTGAA TTGGGACCCT CAGCAGAGAG GAGGACCTGT      780

TGACCTTACT TTGAAGCAGC CAAGATGTTT TGTATTAATG GATCACATTT TGAATTTGAA      840

GATAGTACAC ATCCTAAATA TGACTTCTGC AAAGATAATT TCTTTTCTGT TACCACCTGA      900

TGAAAGTCTT CATTCACTAC AGTCTCGTAT TGAGCGTGAA ACTGGAATAA ATACTGGTTC      960

TCAAGAACTT CTTTCAGAGA CAGGAATTTC TCTGGATCCT CGGAAACCAG CCTCTCAATG     1020

TGTTCTAGAT GGAGTTAGAG GCTGTGATAG CTATATGGTT TATTTGTTTG ATAAAAGTAA     1080

AACTGTATAT GAAGGGCCAT TTGCTTCCAG AAGTTTATCT GATTGTGTAA ATTATATTGT     1140

ACAGGACAGC AAAATACAGC TTCCAATTAT ACAGCTGCGT AAAGTGTGGG CTGAAGCAGT     1200

GCACTATGTG TCTGGACTAA AGAAGACTA TAGCAGGCTC TTTCAGGGAC AAAGGGCAGC     1260

AATGTTAAGT CTTCTTAGAT ATAATGCTAA CTTAACAAAA ATGAAGAACA CTTTGATCTC     1320

AGCATCACAA CAACTGAAAG CTAAATTGGA GTTTTTTCAC AAAAGCATTC AGCTTGACTT     1380

GGAGAGATAC AGCGAGCAGA TGACGTATGG GATATCTTCA GAAAAAATGC TAAAAGCATG     1440

GAAAGAAATG GAAGAAAAGG CCATCCACTA TGCTGAGGTT GGTGTCATTG GATACCTGGA     1500

GGATCAGATT ATGTCTTTGC ATGCTGAAAT CATGGAGCTA CAGAAGAGCC CCTATGGAAG     1560

ACGTCAGGGA GACTTGATGG AATCTCTGGA ACAGCGTGCC ATTGATCTAT ATAAGCAGTT     1620

AAAACACAGA CCTTCAGATC ACTCCTACAG TGACAGCACA GAGATGGTGA AAATCATTGT     1680
```

-continued

| | | | | |
|---|---|---|---|---|
| GCACACTGTG | CAGAGTCAGG | ACCGTGTGCT | CAAGGAGCGT | TTTGGTCATT TGAGCAAGTT | 1740 |
| GTTGGGCTGT | AAGCAGAAGA | TTATTGATCT | ACTCCCTAAG | GTGGAAGTGG CCCTCAGTAA | 1800 |
| TATCAAAGAA | GCTGACAATA | CTGTCATGTT | CATGCAGGGA | AAAAGGCAGA AAGAAATATG | 1860 |
| GCATCTCCTT | AAAATTGCCT | GTACACAGAG | TTCTGCCCGC | TCTCTTGTAG GATCCAGTCT | 1920 |
| AGAAGGTGCA | GTAACCCCTC | AAGCATACGC | ATGGCTGGCC | CCCGACTTAG CAGAACATGA | 1980 |
| TCATTCTCTG | TCATGTGTGG | TAACTCCTCA | AGATGGGGAG | ACTTCAGCAC AAATGATAGA | 2040 |
| AGAAAATTTG | AACTGCCTTG | GCCATTTAAG | CACTATTATT | CATGAGGCAA ATGAGGAACA | 2100 |
| GGGCAATAGT | ATGATGAATC | TTGATTGGAG | TTGGTTAACA | GAATGA | 2146 |